(12) United States Patent
Ran et al.

(10) Patent No.: US 9,735,568 B2
(45) Date of Patent: Aug. 15, 2017

(54) IONIC WIND PURIFIER AND DISCHARGE MONITORING AND PROTECTIVE CIRCUIT OF HIGH-VOLTAGE ION PURIFIER

(71) Applicant: Suzhou BeiAng Technology Ltd., Suzhou (CN)

(72) Inventors: Hongyu Ran, Suzhou (CN); Zhaofeng Wei, Suzhou (CN); Yan Zhang, Suzhou (CN); Yigang Liu, Suzhou (CN)

(73) Assignee: SUZHOU BEIANG TECHNOLOGY LTD., Suzhou (CN)

( * ) Notice: Subject to any disclaimer, the term of this patent is extended or adjusted under 35 U.S.C. 154(b) by 0 days.

(21) Appl. No.: 14/895,243

(22) PCT Filed: Jun. 3, 2014

(86) PCT No.: PCT/CN2014/079113
§ 371 (c)(1),
(2) Date: Dec. 2, 2015

(87) PCT Pub. No.: WO2014/194813
PCT Pub. Date: Dec. 11, 2014

(65) Prior Publication Data
US 2016/0118787 A1    Apr. 28, 2016

(30) Foreign Application Priority Data

Jun. 4, 2013 (CN) .......................... 2013 1 0219059
Jul. 5, 2013 (CN) .......................... 2013 1 0281809

(51) Int. Cl.
*C01B 13/10* (2006.01)
*H01J 7/24* (2006.01)
(Continued)

(52) U.S. Cl.
CPC ................. *H02H 9/04* (2013.01); *A61L 9/22* (2013.01)

(58) Field of Classification Search
CPC ............. C01B 13/11; B01J 19/08; B03C 3/08
(Continued)

(56) References Cited

U.S. PATENT DOCUMENTS 5,192,894 A    3/1993   Teschner
7,150,780 B2 * 12/2006  Krichtafovitch .......... B03C 3/08
                                                     250/423 R
(Continued)

FOREIGN PATENT DOCUMENTS

CN    2038783 U    6/1989
CN    1573243 A    2/2005
(Continued)

OTHER PUBLICATIONS

International Search Report in international application No. PCT/CN2014/079113, mailed on Sep. 1, 2014.
(Continued)

*Primary Examiner* — Monzer R Chorbaji
(74) *Attorney, Agent, or Firm* — Syncoda LLC; Feng Ma; Junjie Feng

(57) ABSTRACT

An ionic wind purifier is described. The ionic wind purifier includes a generating electrode and a collecting electrode, which are arranged oppositely. A potential difference exists between the generating electrode and the collecting electrode, and at least one first projecting part is arranged on each collecting electrode plate of the collecting electrode. The first projecting part has a smooth surface. Thus, by arranging the first projecting part, the adsorption area of the collecting electrode is increased and the absorption capability of the collecting electrode is improved, thereby improving the purification efficiency of the ionic wind purifier and improving the use performance thereof. A discharge monitoring and protective circuit of a high-voltage ion purifier is also described.

18 Claims, 6 Drawing Sheets

(51) Int. Cl.
*B01J 19/08* (2006.01)
*H02H 3/20* (2006.01)
*H02H 9/04* (2006.01)
*A61L 9/22* (2006.01)

(58) Field of Classification Search
USPC .................. 422/186.07; 315/111.21; 55/108; 204/176; 361/91.1; 96/72
See application file for complete search history.

(56) References Cited

U.S. PATENT DOCUMENTS

| | | |
|---|---|---|
| 7,655,076 B2 | 2/2010 | Griffiths |
| 2005/0150384 A1 | 7/2005 | Krichtafovitch |
| 2006/0070526 A1 | 4/2006 | Hong |
| 2008/0034973 A1 | 2/2008 | Griffiths |
| 2012/0044080 A1 | 2/2012 | Zhu |

FOREIGN PATENT DOCUMENTS

| | | |
|---|---|---|
| CN | 1735775 A | 2/2006 |
| CN | 2820328 Y | 9/2006 |
| CN | 101213025 A | 7/2008 |
| CN | 101217320 A | 7/2008 |
| CN | 201120005 Y | 9/2008 |
| CN | 201688515 U | 12/2010 |
| CN | 101954313 A | 1/2011 |
| CN | 102013660 A | 4/2011 |
| CN | 102059681 A | 5/2011 |
| CN | 201988447 U | 9/2011 |
| CN | 102243279 A | 11/2011 |
| CN | 103007329 A | 4/2013 |
| CN | 103008106 A | 4/2013 |
| CN | 202844181 U | 4/2013 |
| CN | 103166194 A | 6/2013 |
| CN | 103263686 A | 8/2013 |
| CN | 103346548 A | 10/2013 |

OTHER PUBLICATIONS

English Translation of the Written Opinion of the International Search Authority in international application No. PCT/CN2014/079113, mailed on Sep. 1, 2014.

* cited by examiner

IONIC WIND PURIFIER AND DISCHARGE MONITORING AND PROTECTIVE CIRCUIT OF HIGH-VOLTAGE ION PURIFIER

CROSS-REFERENCE TO RELATED APPLICATIONS

The present application is a U.S. national stage application under 37 U.S.C. 371 of, and claims priority to, PCT/CN2014/079113 filed on Jun. 3, 2014, which claims priority to Chinese patent application No. 201310219059.5 filed on Jun. 4, 2013, and Chinese patent application No. 201310281809.1 filed on Jul. 5, 2013. The disclosures of these applications are hereby incorporated by reference in their entirety.

TECHNICAL FIELD

In some embodiments, the disclosure relates to the field of indoor purification devices, particularly to an ionic wind purifier. In some embodiments, the disclosure relates to the technical field of electronic circuits, particularly to a discharge monitoring and protective circuit of a high-voltage ion purifier.

BACKGROUND

With the improvement of people's living standards, demands for environment protection and health are also rising. It is urgent to develop an air purifier with high performance so as to purify indoor air and optimize an indoor environment, and ionic wind purifiers are also applied more and more widely in everyday life.

Air passes through a primary filter screen of an air inlet and reaches a generating electrode. The generating electrode forms a plasma field under the action of a high voltage. Protein structures on the surfaces of bacteria and viruses in the air passing through the plasma field are damaged so as to kill the bacteria and the viruses, and harmful organic molecules including formaldehyde and the like are decomposed into water and carbon dioxide under the action of high-energy electrons and strong oxidizing free radicals. A high-voltage electric field of the generating electrode electrically charges some air, and enables the air to move under the action of a force of the electric field to collide with dust particles in the air and electrically charge the dust particles. Like a snowballing effect, more and more air particles are electrically charged. When moving to the vicinity of a collecting electrode with an opposite electric charge, the electrically charged particles are adsorbed by the collecting electrode due to electrostatic adsorption. Those not adsorbed reach a repelling electrode with the same electric charge and are pushed back to the collecting electrode due to a repellent action of the same electric charges, thereby improving a particle clearing effect to above 99%. Besides, the plasma field generates a plasma flow, so as to produce sufficient air speed to circulate indoor air without a fan, thereby saving energy noiselessly.

A typical ionic wind purifier includes an air inlet, an air outlet and a generating electrode and a collecting electrode arranged between the air inlet and the air outlet. The generating electrode and a collecting electrode module (including the collecting electrode and a repelling electrode group) are arranged oppositely.

It may be learned from the working process above that the collecting electrode is one of the core components of the ionic wind purifier. Dust particles in the purifier need to be adsorbed on the surface of the collecting electrode so as to implement purification. Therefore, the absorption effect of the collecting electrode directly affects the purification efficiency of the ionic wind purifier, thus affecting the use performance thereof.

Therefore, it has become a problem to be solved by those skilled in the art to improve the absorption capability of the collecting electrode so as to improve the purification efficiency of the ionic wind purifier and improve the use performance thereof.

Besides, a common purifier purifies air by applying a High Efficiency Particulate Air Purifier (HEPA) or a physical technology including water washing and the like at present, thus having very limited efficiency in removal of inhalable particles, and the absorption effect of an HEPA filter screen attenuates seriously over time after dust is accumulated. Therefore, an existing high-voltage plasma dust collector or a high-voltage electrostatic dust collector has attracted more attention from clients so as to solve the shortcomings of the purifier above.

However, a high-voltage ion purifier is easy to discharge at a high voltage, thus it is necessary to monitor and protect the high voltage discharge in real time during application.

Purifier discharge: a spatial high voltage exists when a high-voltage ion purifier works, the properties of an instantaneous electric field will be changed when particles including dust, flocks and the like having a relatively large particle size fly into the high-voltage electric field, and a cracking discharge sound will be generated; this process is called purifier discharge.

A noise generated when a purifier discharges will affect the use experience of a consumer while continuous discharge will also result in security risk, thus it is necessary to detect and handle a slight discharge in time. Continuous discharge may be avoided if the size of an electric field is adjusted in time according to a discharge condition.

At present, high voltage discharge is mainly monitored by two modes.

In the first mode, a leakage protector is installed directly. The leakage protector is able to detect an extreme condition. In other words, discharge can be detected only when deteriorating continuously to a state close to a short circuit, which is equivalent to short circuit detection.

Apparently, such discharge detection does not have a good protective effect, and when high-voltage discharge is discontinuous, but not continuous, the discharge can be hardly detected and thus protection cannot be implemented in time.

In the second mode, only a discharge signal is detected directly. Discharge protection is implemented only when the discharge signal is higher than a certain reference signal. However, a common discharge signal is weak, and the protection mode can implement effective protection only when intense discharge is generated.

It is a technical problem to be solved by those skilled in the art to provide a discharge monitoring and protective circuit for a high-voltage ion purifier so as to effectively monitor and protect discharge in time.

SUMMARY

The disclosure aims to provide an ionic wind purifier, and a collecting electrode thereof has strong absorption capability, so as to improve the purification efficiency of a plasma flow purifier, and improve the use performance thereof.

The disclosure provides an ionic wind purifier so as to solve the technical problem above, which includes a generating electrode and a collecting electrode, which are arranged oppositely. A potential difference exists between the generating electrode and a collecting electrode module. The collecting electrode module includes the collecting electrode and a repelling electrode. At least one first projecting part is arranged on each collecting electrode plate, and the first projecting part has a smooth surface.

Preferably, the first projecting part may extend along the collecting electrode plate in a direction parallel to the generating electrode.

Preferably, the first projecting part may include an external projecting part and an internal projecting part; the external projecting part and the internal projecting part may be arranged along a width direction of the collecting electrode plate, the external projecting part may be located on an external side of the internal projecting part; and a projecting height of the external projecting part may be higher than that of the internal projecting part.

Preferably, the collecting electrode module may further include the repelling electrode, a repelling electrode plate of the repelling electrode may be arranged at an interval with the collecting electrode plate, and a potential difference may exist between the repelling electrode and the collecting electrode.

Preferably, at least one second projecting part may be arranged on each repelling electrode plate and the second projecting part may have a smooth surface.

Preferably, a ratio of a potential difference to a distance between the repelling electrode plate and the adjacent collecting electrode plate may be less than 1e7V/m.

Preferably, a connection mode among the collecting electrode plates or among the repelling electrode plates may be that relative locations are fixed by a fixing metal sheet and fixed connection is implemented by a conductive adhesive.

Preferably, a connection mode among the collecting electrode plates or among the repelling electrode plates may be that relative locations are fixed by a fixing metal sheet and fixation is implemented by a leaf spring attached to the metal sheet.

Preferably, each collecting electrode plate and each repelling electrode plate may be fixed by folding and extruding the projecting parts on each plate edge.

Preferably, the collecting electrode and the repelling electrode may be connected by an insulating sleeve coated outside of the collecting electrode and the repelling electrode, and the insulating sleeve may have a hollowed-out structure.

Preferably, several bumps may be arranged in a mounting hole of the insulating sleeve, and the bumps may be connected with the collecting electrode plate or with the repelling electrode plate in a pressing manner.

Preferably, the collecting electrode plate and the repelling electrode plate may be made of moldable metal materials, and the collecting electrode plate and the repelling electrode plate may be shaped by an extrusion forming process.

Preferably, the first projecting part may be arranged on an edge of the collecting electrode plate and may be shaped by a stamping and flanging process.

The ionic wind purifier according to the disclosure includes the generating electrode and the collecting electrode, which are arranged oppositely; the potential difference exists between the generating electrode and the collecting electrode, at least one first projecting part is arranged on each collecting electrode plate of the collecting electrode, and the first projecting part has a smooth surface. Thus, by arranging the first projecting part, the adsorption area of the collecting electrode plate is increased and the absorption capability of the collecting electrode is improved, thereby improving the purification efficiency of the plasma flow purifier and improving the use performance thereof.

In a preferred embodiment, the collecting electrode and the repelling electrode of the ionic wind purifier according to the disclosure are connected by an insulating sleeve coated outside of the collecting electrode and the repelling electrode, and the insulating sleeve has a hollowed-out structure, so that a collecting electrode module can be cleaned and then dried in the air. Besides, several bumps are arranged in a mounting hole of the insulating sleeve and the bumps are mounted with the collecting electrode and the repelling electrode in a clamping manner so as to improve the mounting reliability and stability of the collecting electrode and the repelling electrode.

In another specific embodiment, the first projecting part of the ionic wind purifier according to the disclosure may be arranged on an edge of the collecting electrode plate and machine by a stamping and flanging process, thereby simplifying a machining process and lowering machining cost.

Another embodiment of the disclosure provides a discharge monitoring and protective circuit of a high-voltage ion purifier, which can monitor and protect discharge effectively and timely.

Another embodiment of the disclosure provides a discharge monitoring and protective circuit of a high-voltage ion purifier, which includes: a sampling module, a sampling protection module, an output protection module, a shaping module, a comparison amplifier module and a controller.

The sampling module is mounted on positive and negative terminals of a plasma electric field in a high-voltage ion purifier-loaded and configured to sample a discharge signal of the plasma electric field.

The sampling protection module is connected in series on two terminals of the sampling module.

The output protection module is connected in parallel with the sampling module and configured to limit a voltage of the sampling module.

The shaping module is configured to rectify the discharge signal sampled by the sampling module and then transmit the discharge signal to a first input terminal of the comparison amplifier module.

A second input terminal of the comparison amplifier module is connected with a reference signal; the comparison amplifier module compares the discharge signal with the reference signal, amplifies a comparison result and then outputs the comparison result to the controller.

The controller is configured to control a size of the plasma electric field according to the comparison result.

Preferably, the discharge monitoring and protective circuit may further include an attenuation stopper connected on an output terminal of the shaping module.

The attenuation stopper may be configured to stop the comparison result transmitted to the controller from being leaked reversely.

Preferably, the discharge monitoring and protective circuit may further include a pulse width expansion module connected between the attenuation stopper and the controller.

The pulse width expansion module may be configured to perform pulse width expansion on the comparison result and then send the comparison result to the controller.

Preferably, the pulse width expansion module may include a first resistor and a first capacitor, which are connected in parallel with each other.

An output terminal of the pulse width expansion module may be connected with one end of the first resistor and one end of the first capacitor; and the other end of the first resistor and the other end of the first capacitor may be grounded.

The output terminal of the pulse width expansion module may be connected to the controller.

Preferably, the shaping module may be a diode or a rectifier bridge.

Preferably, the reference signal may be obtained by means of logic calculation performed by hardware or may be provided by the controller.

Preferably, the sampling protection module may be a protection clamping component.

Preferably, the output protection module may include two resistors which are a second resistor and a third resistor respectively.

The second resistor may be connected between a positive terminal of the plasma electric field and the sampling module.

The third resistor may be connected between a negative terminal of the plasma electric field and the sampling module.

Preferably, the sampling module may be a resistor having a preset precision.

Preferably, the attenuation stopper may be a diode.

Unlike the related art which can only monitor intense discharge or short circuit discharge, the discharge monitoring and protective circuit according to the embodiment directly mounts the sampling module on two terminals of a load, so as to test discharge signals at the two terminals of the load directly, and compares and amplifies the discharge signals without attenuation, thereby monitoring slight discharge signals on the two terminals of the load. In addition, the circuit according to the disclosure has double protection on the sampling module, so as to avoid an impact of a discharge signal on the sampling module. Therefore, the circuit according to the disclosure can monitor a weak discharge signal in real time, and avoid an abnormality caused by continuous discharge.

DETAILED DESCRIPTION

The core of the disclosure is to provide an ionic wind purifier, and a collecting electrode thereof has strong absorption capability, so as to improve the purification efficiency of a plasma flow purifier, and improve the use performance thereof.

The disclosure will be further expounded hereinafter with reference to the accompanying drawings and specific embodiments so that those skilled in the art may better understand the technical solution of the disclosure.

Figure 1:
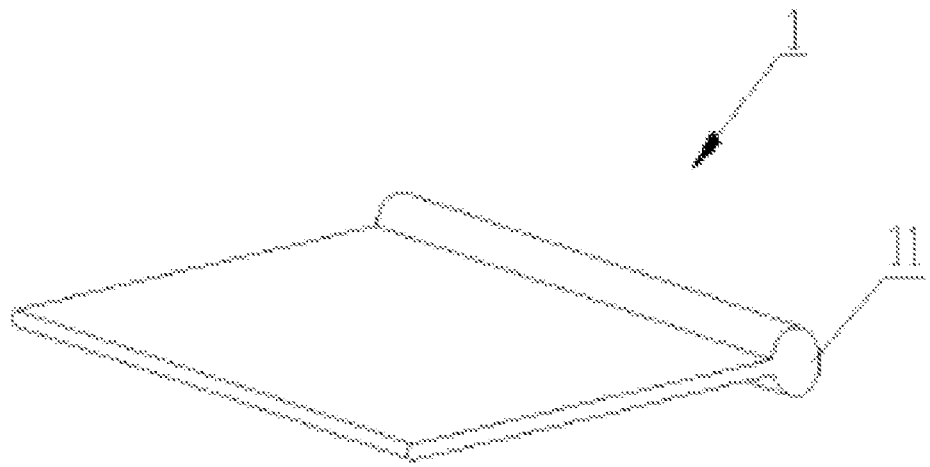
FIG. 1 is a schematic diagram of a first embodiment of a collecting electrode according to the disclosure.
Figure 2:
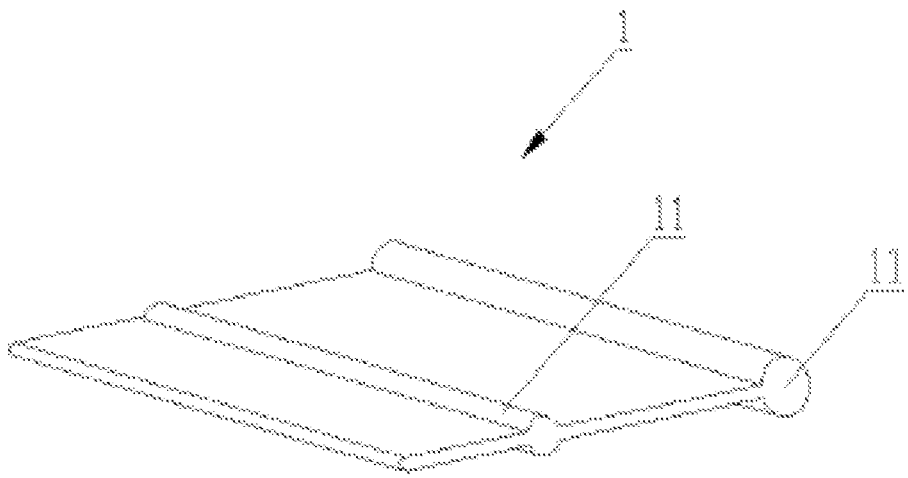
FIG. 2 is a schematic diagram of a second embodiment of a collecting electrode according to the disclosure.
Figure 3:
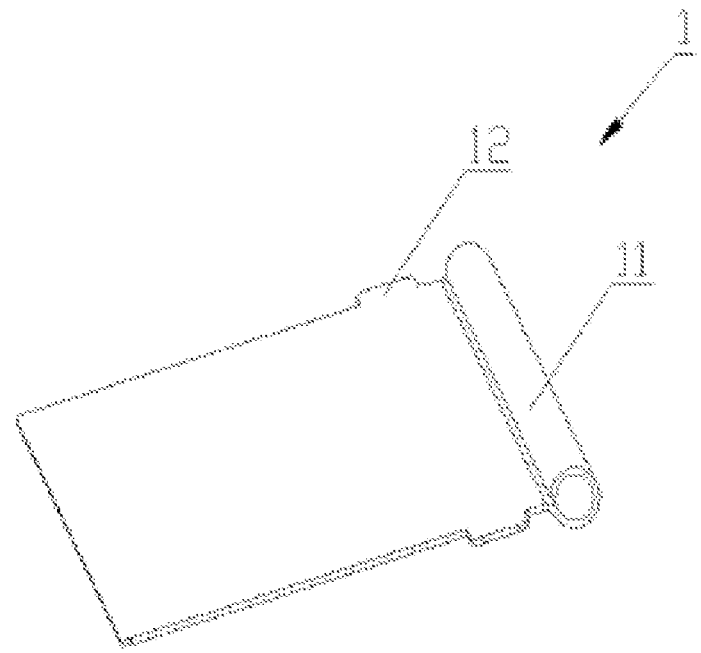
FIG. 3 is a schematic diagram of a third embodiment of a collecting electrode according to the disclosure.

Referring to FIG. 1 to FIG. 3, FIG. 1 is a schematic diagram of a first embodiment of a collecting electrode according to the disclosure, FIG. 2 is a schematic diagram of a second embodiment of a collecting electrode according to the disclosure, and FIG. 3 is a schematic diagram of a third embodiment of a collecting electrode according to the disclosure.

In a specific embodiment, an ionic wind purifier according to the disclosure includes a generating electrode and a collecting electrode, which are arranged oppositely; and a potential difference exists between the generating electrode and the collecting electrode. Besides, at least one first projecting part 11 is arranged on each collecting electrode plate 1 of the collecting electrode, and the first projecting part 11 has a smooth surface. Thus, by arranging the first projecting part 11, the adsorption area of the collecting electrode is increased and the absorption capability of the collecting electrode is improved, thereby improving the purification efficiency of the ionic wind purifier and improving the use performance thereof.

The shape of the first projecting part 11 may be circular, and may be also other shapes having a streamline surface, such as an oval or a wing and so on. The first projecting part 11 may be a bidirectional bump, which means that a projecting structure is provided on two sides of the collecting electrode plate 1, and may be also a unidirectional bump, which means that a projecting structure is provided on a single side of the collecting electrode plate 1.

The first projecting part 11 may be a solid structure as shown in FIG. 1 and FIG. 2, and may be also a hollow structure as shown in FIG. 3.

A plurality of first projecting parts 11 may be provided. The first projecting parts 11 may be arranged in parallel, and may be also arranged in a slightly oblique manner. Each first projecting part 11 may extend along a straight line, may also extend along an arc, and may be even a bump having a smooth surface.

The first projecting part 11 may extend along the width direction of the collecting electrode plate 1. Obviously, the first projecting part 11 is also not limited to extend along the direction, and may incline with a proper angle.

The first projecting part 11 further includes an external projecting part and an internal projecting part. The external projecting part and the internal projecting part are arranged along a direction parallel to the collecting electrode plate 1, and the external projecting part is located on an external side of the internal projecting part. The projecting height of the external projecting part is higher than that of the internal projecting part. The internal projecting part is arranged to prevent air passing through an electric field from flowing too fast, so that the electric field can capture all particles in the air on the collecting electrode plate.

The "external side" refers to a windward side of the collecting electrode plate and the "internal side" refers to a backwind side of the collecting electrode plate.

There may be a plurality of internal projecting parts. The internal projecting parts may have the same projecting height, and may also have different projecting heights.

It needs to be pointed out that the ordinal numerals "first", "second" and the like described herein are used for distinguishing different structures having the same name, but do not represent a certain order, and may not be understood as any limitation.

Figure 4:
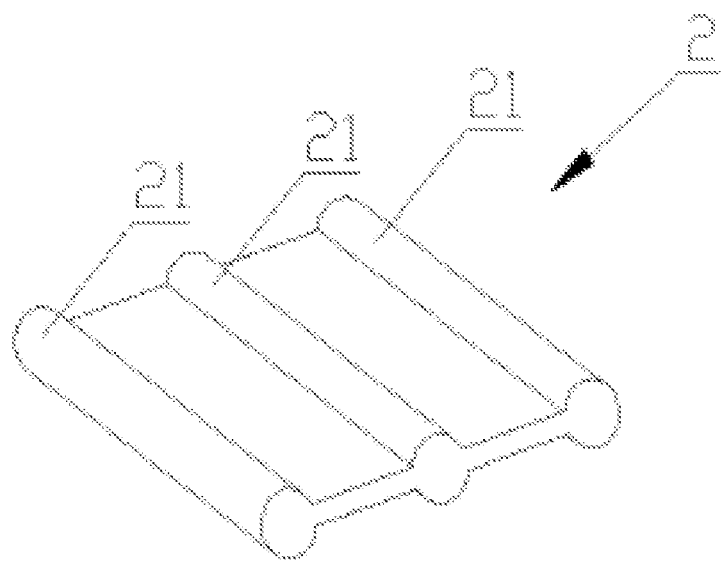
FIG. 4 is a schematic diagram of a first embodiment of a repelling electrode according to the disclosure.
Figure 5:
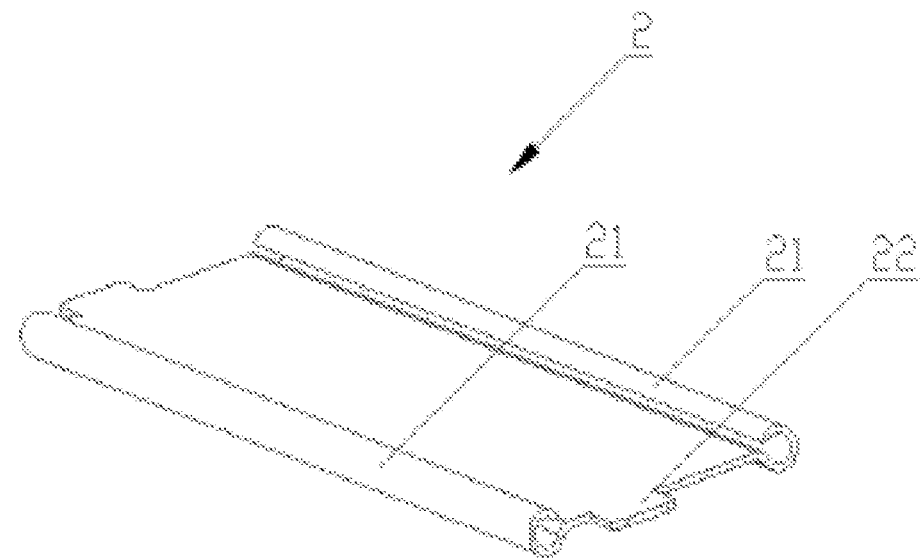
FIG. 5 is a schematic diagram of a second embodiment of a repelling electrode according to the disclosure.

Referring to FIG. 4 and FIG. 5, FIG. 4 is a schematic diagram of a first embodiment of a repelling electrode according to the disclosure, and FIG. 5 is a schematic diagram of a second embodiment of a repelling electrode according to the disclosure.

In the foregoing specific embodiments, the ionic wind purifier according to the disclosure further includes a repelling electrode. A repelling electrode plate 2 of the repelling electrode is arranged at an interval with the collecting electrode plate 1, and the repelling electrode and the generating electrode have the same electric property. The repelling electrode pushes electrically charged particles not adsorbed by the collecting electrode back to the collecting electrode, thereby improving the efficiency of a single filtering process of the ionic wind purifier.

At least one second projecting part 21 is provided on the repelling electrode plate 2 of the repelling electrode and the second projecting part 21 has a smooth surface, so as to increase the area of the repelling electrode, thereby pushing more particles that are not electrically charged back to the collecting electrode to further improve the filtering efficiency of the ionic wind purifier.

The shape of the second projecting part 21 may be circular, and may be also other shapes having a streamline surface, such as an oval or a wing and so on. The second projecting part 21 may be a bidirectional bump, which means that a projecting structure is provided on two sides of the repelling electrode plate 2, and may be also a unidirectional bump, which means that a projecting structure is provided on a single side of the repelling electrode plate 2. The second projecting part 21 may be a solid structure as shown in FIG. 4, and may be also a hollow structure as shown in FIG. 5. When the second projecting part is a hollow structure, it may be manufactured by stamping and flanging a plate material of the repelling electrode plate 2.

A plurality of second projecting parts 21 may be provided. The second projecting parts 21 may be arranged in parallel, and may be also arranged in a slightly oblique manner. Each second projecting part 21 may extend along a straight line, may also extend along an arc, and may be even a bump having a smooth surface.

The second projecting part 21 may extend along the width direction of the repelling electrode plate 2. Obviously, the second projecting part 21 is also not limited to extend along the direction, and may incline with a proper angle.

The second projecting part 21 may also further include an external projecting part and an internal projecting part. The external projecting part and the internal projecting part are arranged along the length direction of the repelling electrode plate 2, and the external projecting part is located on an external side of the internal projecting part. The projecting height of the external projecting part is higher than that of the internal projecting part. The internal projecting part is arranged to prevent the air passing through the electric field from flowing too fast, so that the electric field can push all particles in the air towards the collecting electrode plate.

There may be a plurality of internal projecting parts. The internal projecting parts may have the same projecting height, and may also have different projecting heights.

The ratio of a potential difference to a distance between the repelling electrode plate 2 and the adjacent collecting electrode plate 1 is less than 1e7V/m. Generally, the distance between the repelling electrode plate 2 and the adjacent collecting electrode plate 1 is less than 100 mm, so as to ensure that the electric field between the repelling electrode and the collecting electrode has sufficient intensity.

The collecting electrode plates 1 may be connected by dispensing a conductive adhesive. The conductive adhesive is dispensed to connect all collecting electrode plates, so that each collecting electrode has the same electric properties. A connecting component between the collecting electrode plates 1 may also include a metal strip and a leaf spring arranged in the metal strip. In other words, the collecting electrode plates 1 are connected by a metal strip having a leaf spring to have the same electric properties.

When the collecting electrode plate 1 and the repelling electrode plate 2 are made of a moldable metal including aluminum, stainless steel and the like, the first projecting part 11 may be shaped on the collecting electrode plate 1 by a stamping aluminum extrusion process and the second projecting part 21 may be shaped on the repelling electrode plate 2 by the stamping aluminum extrusion process.

The mounting mode of the collecting electrode is also applicable to the repelling electrode, which will not be repeated here.

Figure 6:
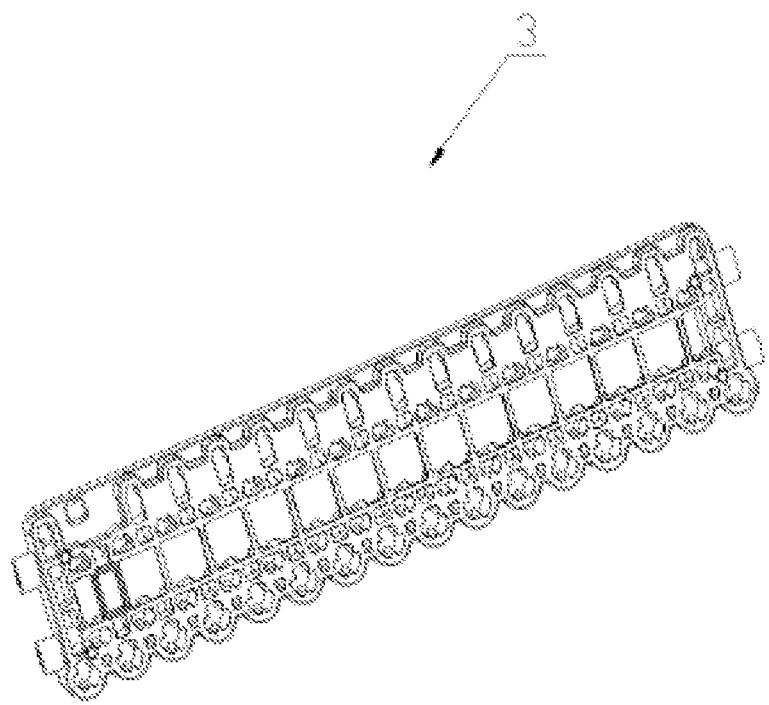
FIG. 6 is a structural diagram of a specific embodiment of an insulating sleeve according to the disclosure.
Figure 7:
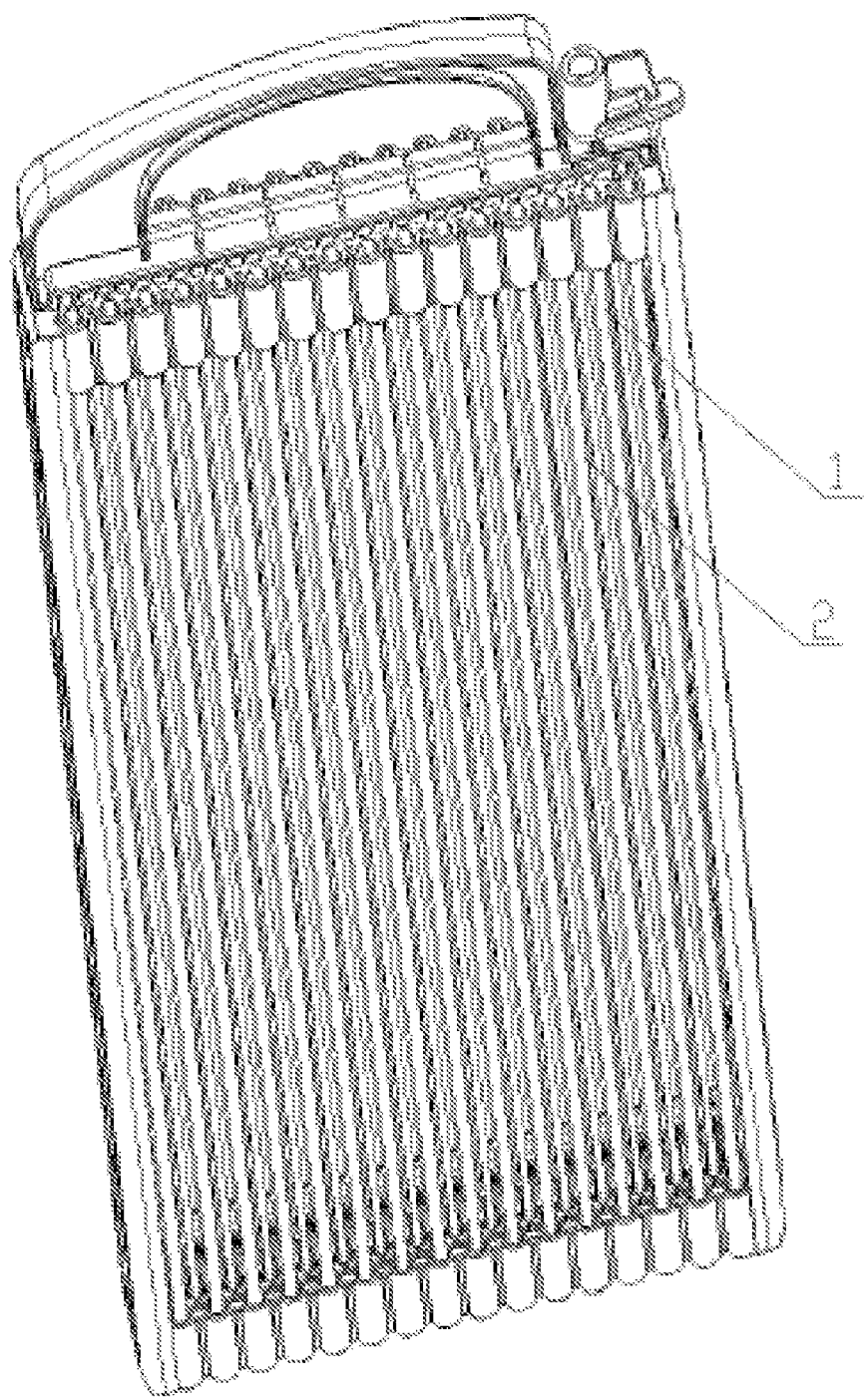
FIG. 7 is a structural diagram of a specific embodiment of a collecting electrode module (including a collecting electrode and a repelling electrode) according to the disclosure.

Referring to FIG. 6, FIG. 6 is a structural diagram of a specific embodiment of an insulating sleeve according to the disclosure.

The collecting electrode and the repelling electrode are connected by an insulating sleeve 3 coated outside of the collecting electrode and the repelling electrode, and the insulating sleeve 3 has a hollowed-out structure. In other words, a through groove is arranged on the insulating sleeve 3, so that it is easier for water to directly flow away along the collecting electrode plate 1 when the collecting electrode module is cleaned, and the collecting electrode plate 1 is easier to be dried, thus reducing the time for the collecting electrode plate 1 to be cleaned and dried in the air. In addition, several bumps are arranged in a mounting hole of the insulating sleeve 3 and the bumps are mounted with the collecting electrode or the repelling electrode in a clamping manner so as to improve the mounting stability of the collecting electrode and the repelling electrode. Several bumps are arranged so that the collecting electrode and the repelling electrode are mounted and fixed by point contact instead of being installed by surface contact during installation, thus the installation is smoother. In the meanwhile, the repelling electrode plate 2 can be electrically charged to increase a creepage distance of a voltage by means of the point contact mode.

As shown in FIG. 3 and FIG. 5, a first clamping block 12 is arranged on the collecting electrode plate 1 of the collecting electrode, and a second clamping block 22 is arranged on the repelling electrode plate 2 of the repelling electrode, so as to install the collecting electrode plate 1 and the repelling electrode plate 2 in a bent manner.

The collecting electrode plate 1 shaped by an aluminum extrusion mould, then a required length is cut, and the first clamping block is cut by a stamping die so that the first clamping block is bent to implement installation. The first projecting part 11 may be shaped by an aluminum extrusion mould and may be also manufactured into the shape of the original collecting electrode plate 1 by a stamping mould, and then shaped by stamping and flanging. The repelling electrode plate 2 may be also stamped by a stamping die and flanged to form the second clamping block. A plurality of cylinders is provided on the repelling electrode plate by a process of performing aluminum extrusion, and then cutting an end face.

Figure 8:
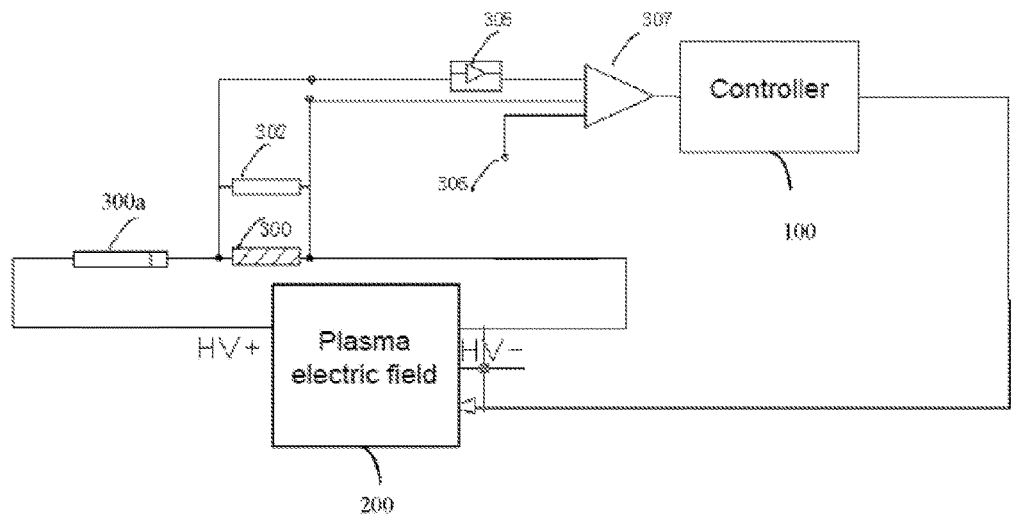
FIG. 8 is a schematic diagram of a first embodiment of a discharge monitoring and protective circuit of a high-voltage ion purifier according to the disclosure.

Referring to FIG. 8, the figure is a schematic diagram of a first embodiment of a discharge monitoring and protective circuit of a high-voltage ion purifier according to the disclosure.

The discharge monitoring and protective circuit of the high-voltage ion purifier according to the embodiment includes: a sampling module 300, a sampling protection module 300a, an output protection module 302, a shaping module 305, a comparison amplifier module 307 and a controller 100.

The sampling module 300 is mounted on positive and negative terminals of a plasma electric field 200 in a high-voltage ion purifier-loaded and configured to sample a discharge signal of the plasma electric field 200.

The sampling module 300 is directly mounted on two terminals of the plasma electric field 200, thereby improving the sampling sensitivity and real time performance compared with a general sampling mode. In this way, discharge of the plasma electric field 200 may be monitored in a more real-time manner, and a response may be made rapidly as soon as the discharge occurs, thus avoiding a cracking discharge sound and a danger.

The sampling protection module 300a is connected in series on two terminals of the sampling module 300.

It needs to be noted that the sampling protection module 300a may be implemented by a rapid stabilivolt, and such a stabilivolt is quick in response with high instantaneous power.

When the plasma electric field 200 has a discharge abnormality, a high-voltage electric field will fluctuate violently, and the sampling protection module 300a can prevent a surge current of the high-voltage fluctuation from directly impacting the sampling module 300.

The output protection module 302 is connected in parallel with the sampling module 300 and configured to limit a voltage of the sampling module 300, thereby preventing the sampling module 300 from being directly damaged by the high-voltage electric field.

The shaping module 305 is configured to rectify the discharge signal sampled by the sampling module 300 and then transmit the discharge signal to a first input terminal of the comparison amplifier module 307.

Since the discharge signal is an alternating signal, the shaping module 305 shapes and reverses the alternating signal so as to shape the alternating signal into a direct current signal, thereby preventing soft damage on front and back devices. The alternating signal, which is positive and negative at times, has a great impact on an electric component, and shortens the service life of the electric component easily over time, thus the output energy efficiency of the sampled discharge signal is also utilized effectively. A negative pulse signal cannot be recognized, and only a positive signal can be recognized if the shaping is not performed. The discharge properties of the plasma electric field 200 are extracted to the largest extent.

A second input terminal of the comparison amplifier module 307 is connected with a reference signal; the comparison amplifier module 307 compares the discharge signal with the reference signal, amplifies a comparison result and then outputs the comparison result to the controller 100.

The comparison amplifier module 307 in the embodiment has a comparison function and an amplification function. The two functions are combined so as to reduce attenuation of the signal. Generally, amplification and comparison are implemented in two or more integrated circuits in the related art, thus causing significant attenuation to a signal. A separate functional sub-module in an integrated circuit is applied in the embodiment, thereby reducing attenuation of the signal, and a weaker discharge signal can be thus detected.

The controller 100 is configured to control a size of the plasma electric field 200 according to the comparison result.

Unlike the related art which can only monitor intense discharge or short circuit discharge, the discharge monitoring and protective circuit according to the embodiment directly mounts the sampling module on two terminals of a load, so as to test discharge signals at the two terminals of the load directly, and compares and amplifies the discharge signals without attenuation, thereby monitoring slight discharge signals on the two terminals of the load. In addition, the circuit according to the disclosure has double protection on the sampling module, so as to avoid an impact of a discharge signal on the sampling module. Therefore, the circuit according to the disclosure can monitor a weak discharge signal in real time, and avoid an abnormality caused by continuous discharge.

Figure 9:
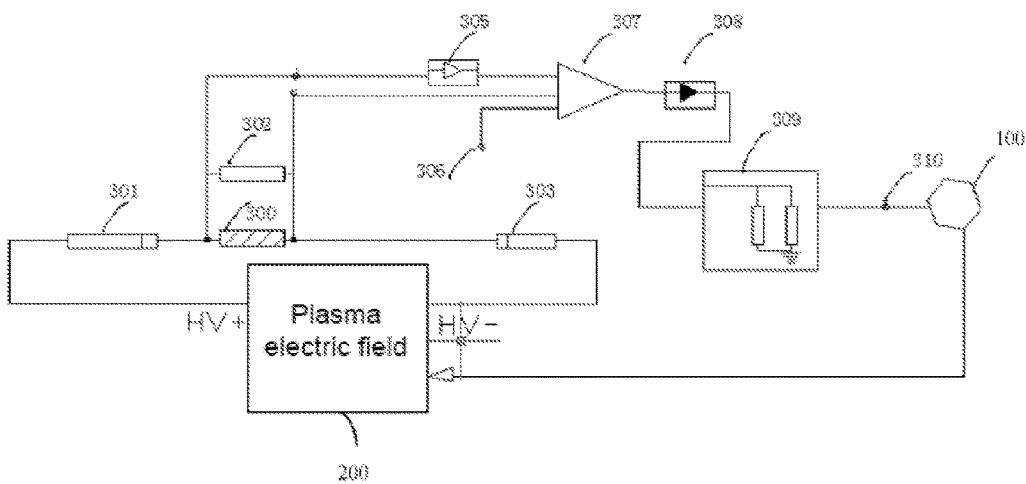
FIG. 9 is a schematic diagram of a second embodiment of a discharge monitoring and protective circuit of a high-voltage ion purifier according to the disclosure.

Referring to FIG. 9, the figure is a schematic diagram of a second embodiment of a discharge monitoring and protective circuit of a high-voltage ion purifier according to the disclosure.

The discharge monitoring and protective circuit of the high-voltage ion purifier according to the embodiment further includes an attenuation stopper 308 connected on an output terminal of the shaping module.

The attenuation stopper 308 is configured to stop the comparison result transmitted to the controller from being leaked reversely.

Preferably, the attenuation stopper 308 may be a diode.

The attenuation stopper 308 may stop a signal 310 outputted to the controller 100 from being leaked reversely, while reducing the effect of interference attenuation of other surrounding devices on the signal 310. In the meanwhile, the attenuation stopper 308 maintains a pulse width signal, thereby reserving sufficient time and space for the controller to read a discharge signal.

The circuit according to the disclosure may further include a pulse width expansion module 309 connected between the attenuation stopper 308 and the controller 100.

The pulse width expansion module 309 is configured to perform pulse width expansion on the comparison result and then to send the comparison result to the controller 100.

Pulse width expansion will be introduced first. Since high-voltage discharge is instantaneous, a signal obtained by the sampling circuit is a pulse signal having a microsecond-level (us) time width, and information of the us-level pulse width signal can be hardly acquired and read by the controller. Thus the pulse width is amplified in time, and a hardware processing process of changing the us level to a millisecond (ms) level is called pulse width expansion.

The pulse width expansion module 309 performs pulse width modulation on a weak discharge signal that is monitored, so that the controller can recognize the weak discharge signal. The controller can hardly recognize the weak signal if the pulse width modulation is not performed. This is also another reason that a discharge detection circuit in the related art fails to detect a weak discharge signal.

The pulse width expansion module 309 is equivalent to a circuit of a resistor-capacitor to implement pulse width modulation by using the delay characteristic of the charge and discharge time, so as to output the signal 310 having an expanded pulse width.

In the embodiment, the output protection module includes two resistors, which are a second resistor 301 and a third resistor 303 respectively.

The second resistor 301 is connected between the positive terminal of the plasma electric field 200 and the sampling module 300.

The third resistor 303 is connected between the negative terminal of the plasma electric field 200 and the sampling module 300.

It needs to be noted that the output protection module may also include a plurality of serial resistors, and may also include one resistor. A specific embodiment of a pulse width expansion module according to an embodiment of the disclosure will be introduced below.

Figure 10:
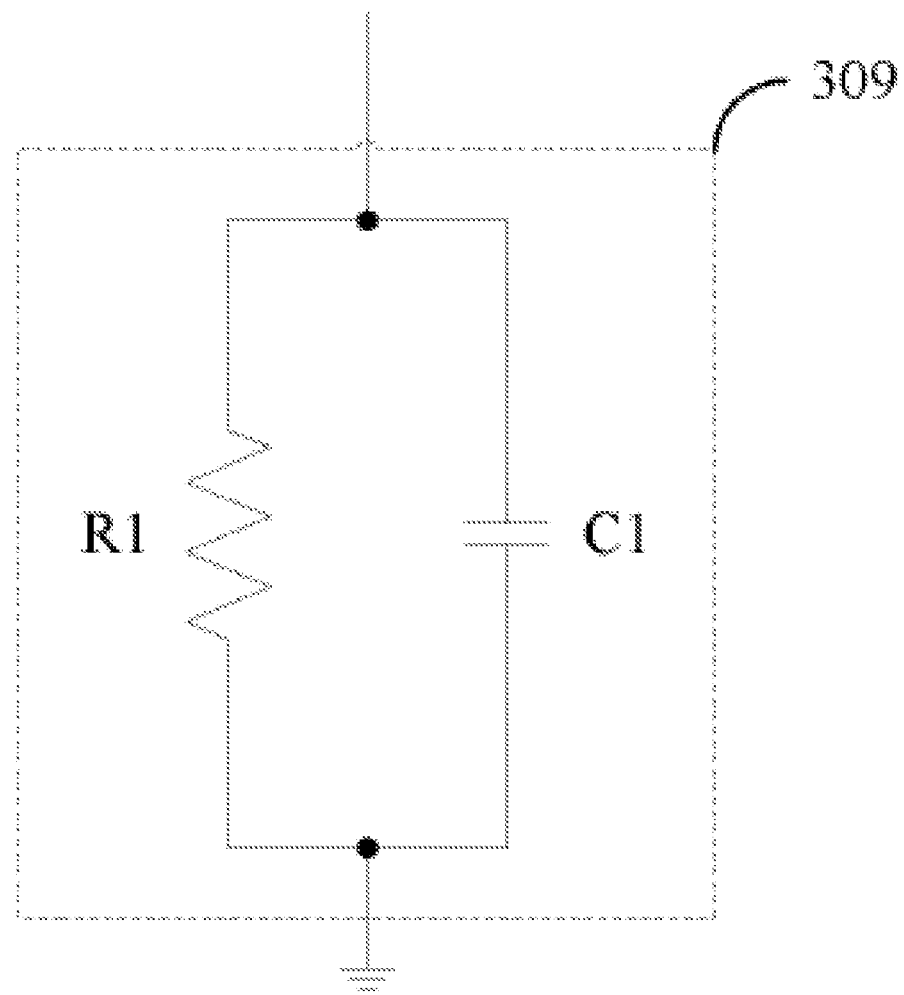
FIG. 10 is a schematic diagram of a pulse width expansion module according to the disclosure.

Referring to FIG. 10, the figure is a schematic diagram of a pulse width expansion module according to the disclosure.

The pulse width expansion module according to the embodiment includes a first resistor R1 and a first capacitor C1, which are connected in parallel.

An output terminal of the pulse width expansion module 309 is connected with one end of the first resistor R1 and one end of the first capacitor C1; and the other end of the first resistor R1 and the other end of the first capacitor C1 are grounded.

It needs to be noted that the output terminal of the pulse width expansion module 309 is connected to an output terminal of the attenuation stopper 308 and an input terminal of the controller 100.

The output terminal of the pulse width expansion module is connected to the controller.

The shaping module in an embodiment of the disclosure may be a diode or a rectifier bridge preferably.

It needs to be noted that the reference signal is obtained by means of logic calculation performed by hardware or is provided by the controller.

It needs to be noted that the sampling protection module is a protection clamping component.

It needs to be noted that the sampling module is a resistor having a preset precision. Generally, the sampling module may be a non-inductive resistor having a precision greater than 5%.

It needs to be noted that the comparison amplifier module 307 according to an embodiment of the disclosure is a high precision rapid comparator. If an input pulse peak value is 0.8V, while the reference signal is 0.7V, then the comparison amplifier module 307 will output a high electrical level. A voltage pulse peak value as high as 5V may be outputted directly by pulling an electric potential on an output terminal of the comparison amplifier module to 5V, for example, and then a 5V signal having an ms-level time span may be obtained by pulse width expansion performed by the pulse width expansion module 309.

What are described above are only preferred embodiments of the disclosure, but are not used for limiting the disclosure in any form. Although the disclosure has been disclosed above by the preferred embodiments, the preferred embodiments are not used for limiting the disclosure. Many possible changes and modifications may be made to the technical solution of the disclosure or the technical solution of the disclosure may be modified into an equivalent embodiment with equivalent changes by means of the method and technical content disclosed above by anyone skilled in the art without departing from the scope of the technical solution of the disclosure. Therefore, all the content not departing form the technical solution of the disclosure, and simple modifications, equivalent changes and modifications made to above embodiments on the basis of the technical essence of the disclosure belong to the protection scope of the technical solution of the disclosure.

The invention claimed is:

1. An ionic wind purifier, comprising a generating electrode and a collecting electrode, which are arranged oppositely; a potential difference exists between the generating electrode and the collecting electrode, wherein at least one first projecting part (11) is arranged on each collecting electrode plate (1) of the collecting electrode, and the first projecting part (11) has a smooth;

the ionic wind purifier further comprising a repelling electrode, a repelling electrode plate (2) of the repelling electrode is arranged at an interval with the collecting electrode plate (1), and a potential difference exists between the repelling electrode and the collecting electrode;

wherein each collecting electrode plate (1) and each repelling electrode plate (2) are fixed by folding and extruding the projecting parts on each plate edge;

wherein the collecting electrode and the repelling electrode are connected by an insulating sleeve (3) coated outside of the collecting electrode and the repelling electrode, and the insulating sleeve (3) has a hollowed-out structure; wherein several bumps are arranged in a mounting hole of the insulating sleeve (3), and the bumps are connected with the collecting electrode plate (1) or with the repelling electrode plate (2) in a pressing manner.

2. The ionic wind purifier according to claim 1, wherein the first projecting part (11) extends along the collecting electrode plate (1) in a direction parallel to the generating electrode.

3. The ionic wind purifier according to claim 2, wherein the first projecting part (11) comprises an external projecting part and an internal projecting part; the external projecting part and the internal projecting part are arranged along a width direction of the collecting electrode plate (1), the external projecting part is located on an external side of the internal projecting part; and a projecting height of the external projecting part is higher than that of the internal projecting part.

4. The ionic wind purifier according to claim 1, wherein at least one second projecting part (21) is arranged on each repelling electrode plate (2), and the second projecting part (21) has a smooth surface.

5. The ionic wind purifier according to claim 4, wherein a ratio of a potential difference to a distance between the repelling electrode plate (2) and the adjacent collecting electrode plate (1) is less than 1e7V/m.

6. The ionic wind purifier claim 1, wherein a connection mode among the collecting electrode plates (1) or among the repelling electrode plates (2) is that relative locations are fixed by a fixing metal sheet and fixed connection is implemented by a conductive adhesive; or wherein a connection mode among the collecting electrode plates (1) or among the repelling electrode plates (2) is that relative locations are fixed by a fixing metal sheet and fixation is implemented by a leaf spring attached to the metal sheet.

7. The ionic wind purifier according to claim 1, wherein the first projecting part (11) is arranged on an edge of the collecting electrode plate (1) and is shaped by a stamping and flanging process.

8. The ionic wind purifier according to claim 1, wherein the hollowed-out structure of the insulating sleeve (3) includes through grooves arranged on the insulating sleeve (3) for facilitating water to directly flow away along each collecting electrode plate (1) when being cleaned.

9. The ionic wind purifier according to claim 1, wherein the bumps are connected with the collecting electrode plate (1) or with the repelling electrode plate (2) in a pressing manner, so that the collecting electrode and the repelling electrode are mounted and fixed by point contact instead of being installed by surface contact;
wherein the repelling electrode plate (2) is electrically charged to increase a creepage distance of a voltage by means of the point contact.

10. A discharge monitoring and protective circuit of a high-voltage ion purifier, comprising: a sampling module, a sampling protection module, an output protection module, a shaping module, a comparison amplifier module and a controller;
the sampling module is mounted on positive and negative terminals of a plasma electric field in a high-voltage ion purifier-loaded and configured to sample a discharge signal of the plasma electric field;
the sampling protection module is connected in series on two terminals of the sampling module;
the output protection module is connected in parallel with the sampling module and configured to limit a voltage of the sampling module;
the shaping module is configured to rectify the discharge signal sampled by the sampling module and then transmit the discharge signal to a first input terminal of the comparison amplifier module;
a second input terminal of the comparison amplifier module is connected with a reference signal; the comparison amplifier module compares the discharge signal with the reference signal, amplifies a comparison result and then outputs the comparison result to the controller;
the controller is configured to control a size of the plasma electric field according to the comparison result.

11. The discharge monitoring and protective circuit of the high-voltage ion purifier according to claim 10, further comprising an attenuation stopper connected on an output terminal of the shaping module;
the attenuation stopper is configured to stop the comparison result transmitted to the controller from being leaked reversely.

12. The discharge monitoring and protective circuit of the high-voltage ion purifier according to claim 11, further comprising a pulse width expansion module connected between the attenuation stopper and the controller;
the pulse width expansion module is configured to perform pulse width expansion on the comparison result and then send the comparison result to the controller.

13. The discharge monitoring and protective circuit of the high-voltage ion purifier according to claim 12, wherein the pulse width expansion module comprises a first resistor and a first capacitor, which are connected in parallel with each other;
an output terminal of the pulse width expansion module is connected with one end of the first resistor and one end of the first capacitor; and the other end of the first resistor and the other end of the first capacitor are grounded;
the output terminal of the pulse width expansion module is connected to the controller.

14. The discharge monitoring and protective circuit of the high-voltage ion purifier according to claim 10, wherein the shaping module is a diode or a rectifier bridge.

15. The discharge monitoring and protective circuit of the high-voltage ion purifier according to claim 10, wherein the reference signal is obtained by means of logic calculation performed by hardware or is provided by the controller.

16. The discharge monitoring and protective circuit of the high-voltage ion purifier according to claim 10, wherein the sampling protection module is a protection clamping component.

17. The discharge monitoring and protective circuit of the high-voltage ion purifier according to claim 10, wherein the output protection module comprises two resistors which are a second resistor and a third resistor respectively;
the second resistor is connected between a positive terminal of the plasma electric field and the sampling module;
the third resistor is connected between a negative terminal of the plasma electric field and the sampling module.

18. The discharge monitoring and protective circuit of the high-voltage ion purifier according to claim 17, wherein the sampling module is a resistor having a preset precision.

* * * * *